United States Patent [19]

Reif et al.

[11] Patent Number: 4,531,402
[45] Date of Patent: Jul. 30, 1985

[54] APPARATUS AND METHOD FOR MEASURING THE CONCENTRATION OF LARGE PARTICLES IN A GAS

[75] Inventors: Robert B. Reif, Grove City; Loren R. Albrechtson, Gahanna, both of Ohio

[73] Assignee: Battelle Development Corp., Columbus, Ohio

[21] Appl. No.: 490,533

[22] Filed: May 2, 1983

[51] Int. Cl.³ .............................. G01N 15/02
[52] U.S. Cl. .......................... 73/28; 55/270; 324/464
[58] Field of Search .................. 73/28, 432 PS; 324/71.4, 454, 464; 340/627; 60/39.091; 55/103, 104, 105, 140, 146, 150, 270, 155

[56] References Cited

U.S. PATENT DOCUMENTS

| | | | |
|---|---|---|---|
| 3,478,494 | 11/1969 | Lustenader et al. | 55/146 |
| 3,493,109 | 2/1970 | Carta et al. | 55/103 |
| 3,697,973 | 7/1972 | Smith, Jr. et al. | 73/28 |
| 3,718,029 | 2/1973 | Gourdine et al. | 73/28 |
| 3,784,902 | 1/1974 | Huber | 73/28 |
| 4,275,353 | 6/1981 | Yang et al. | 324/454 |
| 4,312,180 | 1/1982 | Reif et al. | 73/28 |
| 4,376,637 | 3/1983 | Yang | 55/105 |

FOREIGN PATENT DOCUMENTS 1269818  4/1972  United Kingdom .

OTHER PUBLICATIONS

H. L. Bullock, New Horizons in Electrostatic Separation, 1965, Bulletin of the Bullock-Simpson National Engineering Company.
Electrostatic Separator Handles Nonconductors, Jul. 5, 1965, Chemical and Engineering News, pp. 40-41.
S. Kittaka et al., "Method for Measuring Charging Tendency of Powder in Pneu. Conveyance Through Metal Pipes", Jour. Electrostatics, vol. 6, No. 2, pp. 181-190, 1979.

Primary Examiner—Stephen A. Kreitman
Attorney, Agent, or Firm—Sidney W. Millard

[57] ABSTRACT

The invention provides apparatus and method for measuring the concentration of large particles in a gas which may also contain small particles. The apparatus comprises a triboelectric charging means which effects triboelectric charging of the large particles in the gas, and charge measuring means for measuring charges on the particles in the gas after it has passed the triboelectric charging means. The triboelectric charging means can be a curved section of an air intake duct or the compressor of a turbocharger. The apparatus enables the operation of an engine or other air consuming device to be interrupted when the concentration of large particles in the incoming air is sufficient to damage the engine, but avoids unnecessary shutdowns due to the presence of small particles, e.g. smoke particles, which are too small to damage the engine or other device.

22 Claims, 3 Drawing Figures

APPARATUS AND METHOD FOR MEASURING THE CONCENTRATION OF LARGE PARTICLES IN A GAS

BACKGROUND OF THE INVENTION

This invention relates to an apparatus and method for measuring the concentration of large particles in a gas. Such particles may comprise, for example, dust, soot, solid pollutants and the like. The apparatus and method of the invention are especially intended for protecting engines and other gas receiving devices from damage caused by the intake of air containing too much dust or other particulate matter of such size as to cause engine damage. However, the instant apparatus and method have a variety of other applications; for example, they may be used for checking the efficiency of dust removal equipment used in certain environmental control systems (e.g. removal of fibers from the air in textile mills or removal of dust in grain elevators) or for monitoring environmental pollution by checking the levels of particulate materials in waste gases such as flue gases, automobile exhaust systems, cement kilns and power generation plants.

Internal combustion engines used to power tanks and other vehicles require a large supply of clean air to ensure maximum engine performance and engine life and to reduce maintenance requirements. Air cleaning systems have been developed which will remove 99% of the particulate matter which is drawn into the air intake system. Such high efficiency air cleaning systems are multi-stage units which include barrier type air filters. However, a simple dust leak in the air cleaning system (caused by, for example, accidental perforation of one of the air filters) can negate the effectiveness of the system. The vehicle operator must know when such a leak occurs so that he can shut off the engine and take steps to correct the leak problem before irreparable damage is done. This problem is especially of concern on military tanks equipped with gas turbine engines which are highly susceptible to damage by dust in the air under some operating conditions. Also, problems with excessively dusty air may be encountered in other internal combustion engines equipped with turbo chargers. A reliable dust detection system can also be valuable on any engine and on many other systems where filters are used to remove dust from the air, either to provide a supply of clean air for a particular device or area or to control dust emissions for a manufacturing operation or power generation system.

Several systems have been devised for measuring the concentration of particles in a gas. One such system is described in our U.S. Pat. No. 4,312,180 issued Jan. 26, 1982. This apparatus passes particulate-carrying gas past first and second electrically conductive members spaced apart in a first region so as to provide a potential gradient in part of the region between the first and second members of at least about 30 kilovolts per centimeter. The first and second members thus form a corona and produce ions that charge a substantial proportion of the particles in the gas. Third and fourth electrically conductive members are spaced apart in a second region downstream from the first region and an electrical potential is applied between the third and fourth members so as to provide a potential gradient of substantially less than 30 kilovolts per centimeter therebetween. The charged particles produced in the first region are attracted to either the third or fouth electrically conductive member and there release their charge so that the current flowing from the third and fourth electrically conductive members measures the concentration of particulate matter in the gas.

Another prior art apparatus for measuring the concentration of particles in a gas is described in U.S. Pat. No. 3,679,973 issued July 25, 1972 to N. S. Smith et al. In this prior art apparatus, the particulate-carrying gas is passed through a narrow throat, within which is located an ionizer which serves to charge the particles in the gas in substantially the same way as the first and second electrically conductive members in our own prior art apparatus described above. The air carrying the particles thus charged emerges from the throat into a wider duct, thereby reducing the rate of flow of the gas along the duct. The walls of the wide duct are formed of a plurality of cylindrical, electrically-conductive members insulated from one another and each connected to a separate current measuring device. The reduction in flow velocity along the duct permits the particles to move radially of the duct onto the electrically-conductive members forming the walls of the duct, where they give up their charge to the electrically-conductive members, thereby causing a current flow through each measuring device. By measuring the current flow through the various current measuring devices, the concentration and size of the particles in the gas flow can be measured. This prior art apparatus is complicated; the specific apparatus shown in the drawings of the patent requires four separate electrically-conductive members with associated insulators therebetween, four measuring devices and the voltage source necessary to charge the particles in the throat.

A further apparatus for measuring the concentration of particles in a gas is described in our co-pending application Ser. No. 490,534 of even date herewith entitled "Apparatus and Method for Measuring the Concentration of Particles in a Gas", the disclosure of which is herein incorporated by reference. This co-pending application describes apparatus having a conduit defined by electrically-conductive walls and through which the gas can flow, an electrode protruding into this conduit and insulated from the walls of the conduit and current measuring means or pulse counting means electrically connected to the electrode. The electrode and the conduit member are maintained at substantially the same potential. The flow of particulate-carrying gas along the conduit causes a current to flow from the electrode through the current measuring means or pulse counting means, the magnitude of this current (or the pulse rate therein) measuring the concentration of particles in the gas.

These three types of prior art apparatus described above all rely upon measuring electrical charge upon the particles in the gas. Other types of prior art apparatus for measuring concentration of particles in a gas include light scattering monitors and densitometer-type smoke meters.

Most of the aforementioned types of prior art apparatus for measuring the concentration of particles in a gas suffer from the disadvantage that they do not distinguish between large and small particles in the gas. Most engines and many other gas-using devices can tolerate the presence of very small particles (such as those found in many smokes) but are highly susceptible to damage by relatively large particles (typically those exceeding 5 microns in diameter). Thus, if one fits an engine or similar gas-using device with an apparatus for measuring the concentration of particles in the air entering the engine or other device and this apparatus does not distinguish between large and small particles, the particle-measuring apparatus will yield a considerable number of "false alarms" when the incoming air contains small particles which are sufficient to actuate the particle-measuring apparatus but which would not actually be harmful to the engine or other device. Such false alarms are obviously undesirable since they unnecessarily increase the down time of the engine or other device and may result in unnecessary maintenance costs. This problem of false alarms is exacerbated by the fact that the air filtration system of an engine or other device which is not harmed by very small particles will often, in order to present as little resistance to air flow as possible, be designed so that such very small particles pass the air filtration system and only the larger, potentially damaging particles are retained by the system. Furthermore, most particle-measuring systems which rely upon measuring the electrical charge upon the particles in the gas are especially susceptible to giving false alarms caused by very small particles, since small particles tend to acquire a much larger charge relative to their mass than large particles. Although the apparatus described in the aforementioned U.S. Pat. No. 3,679,973 is capable of measuring the size of particles in a gas flow, it is, as already mentioned, a highly complex apparatus, and the complicated calculations necessary to determine particle sizes using this apparatus render it entirely unsuitable for routine use in applications such as motor vehicles. Light scattering types of particle monitors do possess some capacity to distinguish different size particles, but tend to be insufficiently robust for use in applications such as motor vehicles.

It will thus be seen that there is a need for a simple, robust apparatus for measuring the concentration of large particles in a gas which can distinguish such large particles from much small particles. This invention seeks to provide such an apparatus.

SUMMARY OF THE INVENTION

The invention provides apparatus for measuring the concentration of large particles in a gas comprising triboelectric charging means for effecting triboelectric charging of the large particles in the gas and charge measuring means for measuring charges on the particles in the gas after the gas has passed the triboelectric charging means.

The invention also provides a method of measuring the concentration of large particles in a gas comprising passing the gas through a triboelectric charging means, thereby effecting triboelectric charging of the large particles in the gas and thereafter measuring the charges on the particles in the gas.

The term "triboelectric charging means" is used herein in its conventional sense in the art to mean any device which will cause charging of particles in the gas by friction resulting from contact between such particles and solid surfaces of the triboelectric charging means. For reasons explained below, triboelectric charging means are more effective in charging large particles than small particles and thus the instant apparatus and method are able to measure the concentration of large particles in the gas without excessive interference from the presence of small particles therein.

DETAILED DESCRIPTION OF THE INVENTION

As already mentioned, the apparatus and method of the invention are capable of measuring the concentration of large particles in a gas despite the presence of smaller particles therein. As will be seen from the detailed discussion of the triboelectric charging mechanism given below with reference to FIG. 1, triboelectric charging does not suddenly cease to charge particles at one specific particle size, but the charging effected does decrease rapidly with decreasing particle size. Furthermore, the rate of decrease in triboelectric charging with decreasing particle size will vary somewhat depending upon the exact type of triboelectric charging means employed. Thus, no precise lower size limit can be specified for the large particles, the concentration of which is measured by the instant apparatus and method. However, a typical apparatus of the invention such as might be employed in the air intake system of a vehicle engine will measure the concentration of particles having diameters in excess of about 5 microns and will, for practical purposes, ignore particles having diameters less than about 2 microns.

The charge measuring means of the instant apparatus may have the form of either a current measuring means or a pulse measuring means. Although the two variants of the invention using current measuring means and pulse counting means respectively are very similar in construction, their respective modes of operation are somewhat different and they will therefore be discussed separately below. The form of the instant apparatus using a pulse detecting means (hereinafter referred to as the "instant pulse counting apparatus") does not rely upon the particles actually contacting an electrode and giving up their charge to the electrode, unlike the prior art apparatus mentioned above; instead, in the instant pulse counting apparatus charged particles approaching the electrode induce a charge on the electrode which can be measured by a sensitive electrometer. As the charged particle passes the electrode, the induced charge on the electrode will be approximately equal to the charge on the particle and the induced current in the electrometer will drop to zero. Finally, once the charged particle has passed the electrode, the induced charge on the electrode begins to diminish and eventually drops to zero, thereby producing a current through the electrometer in the opposite direction to the current produced as the particle approaches the electrode. Thus, each separate charged particle or group of charged particles produce two pulses of opposite polarity as they pass the electrode, and these pulses can be measured by a conventional electronic pulse measuring circuit to indicate the concentration of dust in the gas stream.

However, one potentially serious disadvantage of the instant pulse counting apparatus is that a cloud of dust bearing substantially uniform charges will produce only a single pulse as the leading edge of the cloud first approaches the electrode and a single pulse as the trailing edge of the dust cloud leaves the electrode. Thus, to accurately measure the concentration of dust particles in a gas stream containing many such particles, the pulse counting means may be required to be of a relatively complicated type which can take account not only of the number of pulses generated but also of the interval between the two spaced pulses of opposite polarity produced by a dust cloud, with some form of integration device to calculate the total number of dust particles passing the electrode in such a cloud. Fortunately, if the instant pulse counting apparatus is only to be used to detect failure of a filter arrangement in a vehicle air intake system, such refinements may be unnecessary; dust clouds of uniform charge concentration are comparatively rare, the charge concentrations within such a dust cloud tending to vary and thus produce many pulses, so that if the apparatus is only to be used on a "yes/no basis" to detect failures in the air filtration system of a vehicle, relatively simple pulse detecting means should normally yield sufficiently good information.

The baseline output of the electrometer circuit used for detecting the pulses in the instant pulse counting apparatus steadily drifts in the same direction as the charge on the particles. When the electrometer circuit is modified so as to filter out the relatively high frequency pulses (thereby effectively converting the electrometer circuit to a current measuring circuit), it is found that the current measuring circuit shows a steady current dependent upon the large particle concentration in the gas stream. It appears that, although the instant apparatus does not employ any strong electric field such as that employed in our aforementioned earlier U.S. Pat. No. 4,312,180 to force particles into contact with the detecting electrode, the space charge field produced by the charged particles passing along the conduit is sufficient to force the charged particles toward the walls of the conduit and to deposit them upon the electrode. This form of the apparatus of the invention, which employs a pulse measuring means rather than a pulse counting means, will hereinafter be referred to as the "instant current measuring apparatus" and is presently the preferred form of this invention.

The triboelectric charging means used in the instant apparatus can be of various types. This triboelectric charging means may have the form of a conduit member having walls defining a conduit through which the gas can flow, at least part of this conduit being curved. Thus, to incorporate the instant apparatus into an air intake system of an engine which already has a curved conduit member in its air intake, it is only necessary to install an appropriate charge measuring means downstream of the curved conduit member. Alternatively (or in addition) the triboelectric charging means may comprise a conduit member having walls defining a conduit through which the gas can flow and a rotatable member, for example a fan or other similar gas impelling device, disposed within this conduit. In particular, the impeller of a turbocharger functions as an effective triboelectric charging means. Thus, to provide the air intake system of a turbocharged engine with an apparatus of the invention, it is only necessary to install a charge measuring means between the impeller of the existing turbocharger and the engine itself.

Figure 1:
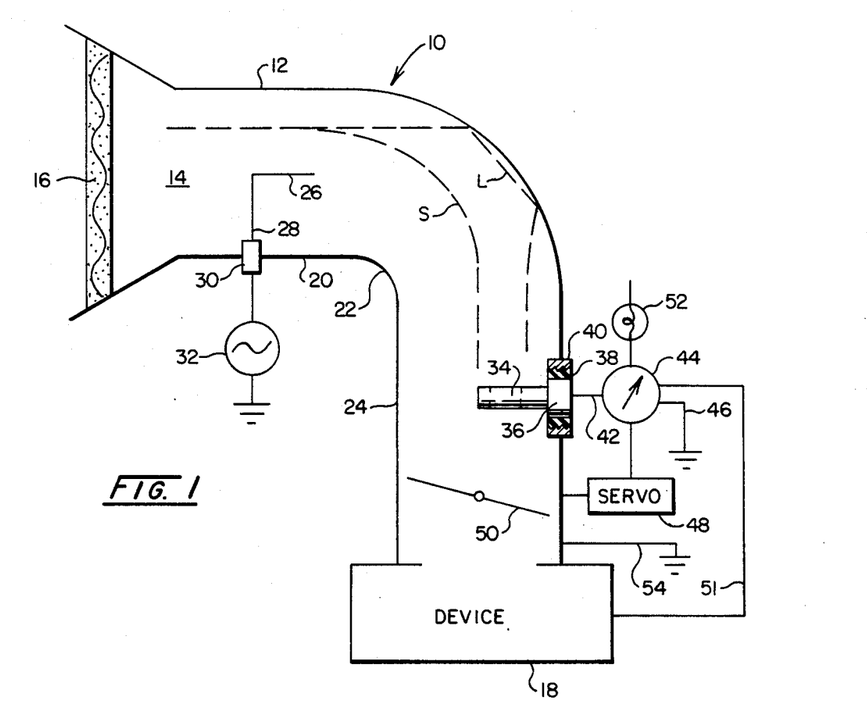
FIG. 1 is a highly schematic section through a first apparatus of the invention.
Figure 2:
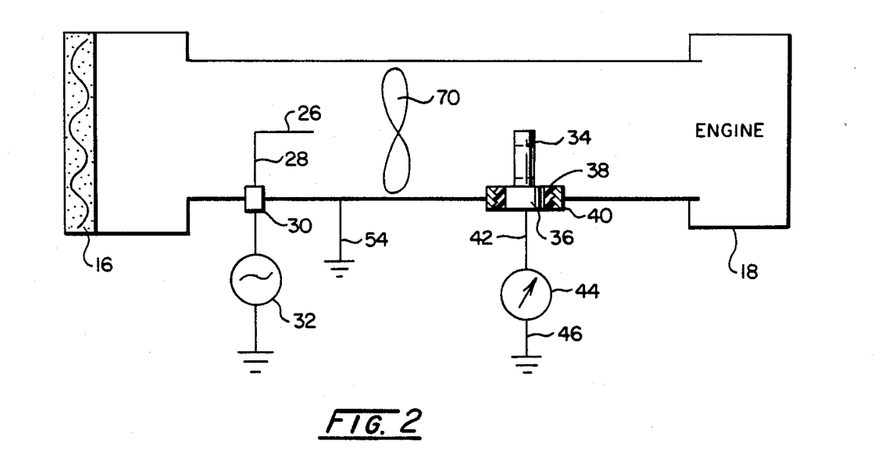
FIG. 2 is a highly schematic section through a second apparatus of the invention.
Figure 3:
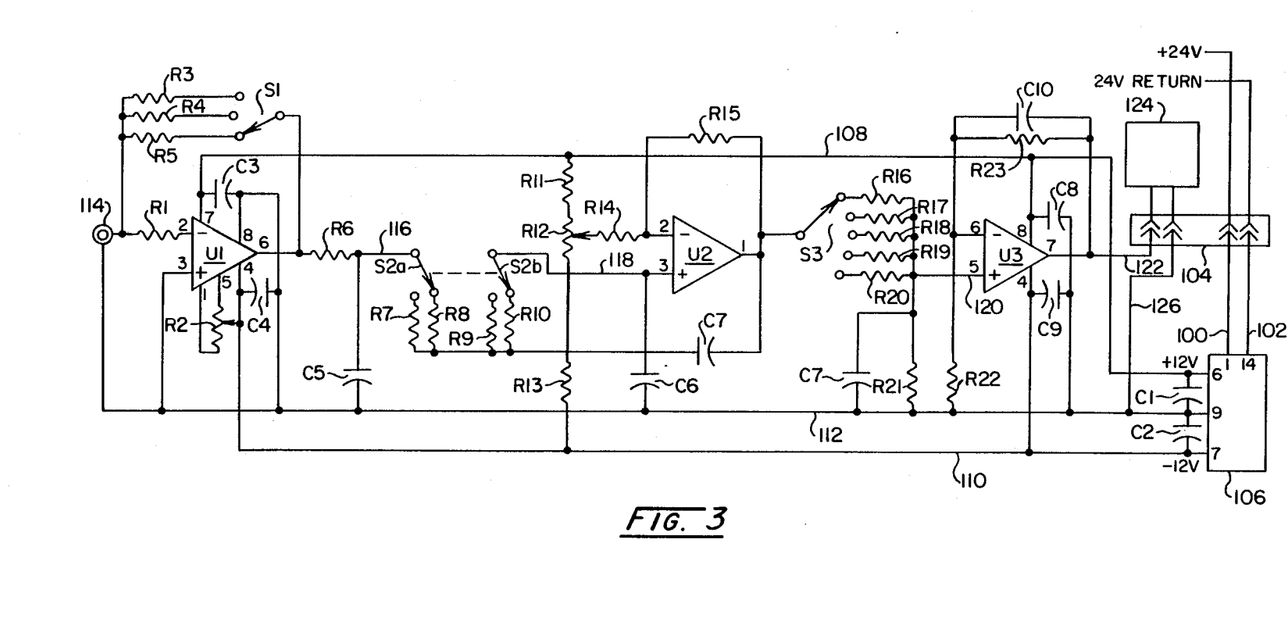
FIG. 3 is a partial circuit diagram of the current measuring device shown in FIG. 1.

The charge measuring means of the instant apparatus can be any device which is effective to measure the concentration of charge in a gas flow. For example, the charge measuring means may be of the form described in our aforementioned U.S. Pat. No. 4,312,180, or of the type described in our aforementioned copending application Ser. No. 490,534; FIGS. 1, 2 and 3 illustrate the latter type of charge measuring means. Those skilled in the art will be aware of other types of charge measuring means which can also be used in the instant apparatus and method.

In order for the instant apparatus to accurately measure the concentration of large particles in the gas, it is of course necessary that the charges measured by the charge measuring means be substantially those placed upon the particles by the triboelectric charging means. We have found that often natural dust and similar particles already bear substantial charges and thus unless these natural charges are neutralized before the particles enter the triboelectric charging means, the readings from the charge measuring means will be inaccurate. Accordingly, the instant apparatus preferably includes a charge neutralizing device for neutralizing pre-existing charges of particles in the gas before the gas passes the triboelectric charging means, this charge neutralizing device conveniently being an alternating current ionizer.

As already mentioned, the instant apparatus may be used in an air filtering system to check that the filtering system is performing properly. Thus, the instant apparatus may include a filter for removing particles from the gas flow before the gas flow passes its electrode. The instant apparatus may also comprise a gas receiving device which receives the gas flow after the gas flow has passed the charge measuring means and current response means for preventing damage to the gas receiving device whenever the charge passing the charge measuring means exceeds a predetermined value. Such a current response means may typically take the form of a servo mechanism responsive to the charge measuring means and arranged to take action to prevent damage to the gas receiving device whenever the charge measuring means indicates the presence of a predetermined concentration of particles in the gas flow past the electrode. For example, when the gas receiving device is an engine, the current response means may typically comprise a valve for blocking the flow of gas from the electrode to the engine and may also include means for stopping the engine, e.g. by interrupting the high tension current in the case of an engine relying upon spark ignition, or by interrupting the fuel supply in the case of a diesel engine. It is desirable that the current response means also include means for providing a warning signal such as a visible or audible alarm; when the instant apparatus is being used in a vehicle, it is of course desirable that a visible alarm be placed on the dashboard adjacent the normal instruments so that it will be readily visible to the driver.

Where the instant apparatus is employed in an air intake system with a filter or other dust-removing device which is subject to failure, and the charge measuring means employs an electrode projecting in the air stream, upon failure of the filter the gas containing a very large concentration of particles may pass the electrode, with the risk that substantial quantities of particles may be deposited upon the electrode. Although the quantity of dust particles deposited upon the electrode after a single filter failure is not likely to greatly affect the operation of the electrode, after repeated filter failure, a sufficiently large quantity of dust particles may be deposited upon the electrode to reduce the sensitivity and/or reproducibility of operation of the apparatus.

Accordingly, it is recommended that after each filter failure the electrode be inspected and, if necessary, cleaned to insure proper operation of the instant apparatus.

The first embodiment of the invention shown schematically in FIG. 1 of the accompanying drawings is a vehicle air intake system. The apparatus (generally designated 10) comprises a conduit member or pipe 12 formed of steel and having a conduit 14 through which air flows from an air filter 16 to a gas receiving device, which in this case has the form of an engine 18. The pipe 12 has three sections, namely a straight, cylindrical section 20 adjacent the air filter 15, a curved section 22 lying downstream of the section 20 and serving as the triboelectric charging means of the apparatus, and a straight, cylindrical section 24 lying downstream of the curved section 22 adjacent the engine 18. The section 20 of the pipe 12 is provided with an alternating current ionizer comprising a needle 26 disposed axially within the section of the conduit 14 lying within the pipe section 20, a support member 28 which holds the needle member 26 in position and which passes through the wall of the pipe section 20, being insulated therefrom by an insulator 30, and a source 32 of alternating current.

An electrode 34 is mounted in an aperture in the wall of the third section 24 of the pipe 20, by means of a cylindrical insulator 36, which serves to electrically insulate the electrode 34 from the metal wall of the pipe 12. The cylindrical wall of the insulator 36 is fixedly attached to a cylindrical metal sleeve 38, which surrounds the insulator 36 and bears an external screw thread. This external screw thread engages a corresponding internal screw thread within a cylindrical sleeve 40 welded to and extending radially of the pipe section 24. The screw thread engagement between the two sleeves 38 and 40 permits the electrode 34 to be readily removed from the pipe section 24 when this is desirable for cleaning or replacement of the electrode 34.

A wire 42 extends from the electrode 34 through the insulator 36 to a current measuring device 44 located outside the pipe 12, the side of the current measuring device remote from the electrode 34 is grounded by a line 46. The current measuring device 44 controls a current response means in the form of a servo mechanism 48 which is arranged to close a butterfly valve 52 disposed within the conduit 14 between the electrode 34 and the engine 18 when the current through the current measuring device 44 exceeds a predetermined value. The current measuring device 44 is also connected to a line 51, which can be used to shut down the engine 18, e.g. by interrupting an ignition circuit therein, and to a warning lamp 52 disposed in the dashboard of the vehicle on which the apparatus is mounted. The pipe 12 is itself grounded by a line 54.

The charge measuring means located within the pipe section 24 has the form shown in FIGS. 1 and 2 of our aforementioned application Ser. No. 490,534. Thus, the electrode 34 has the form of an elongate, cylindrical rod approximately equal in length to the radius of the cylindrical conduit 14 and extends radially of this conduit (i.e. perpendicular to the gas flow along the conduit 14) so that the free end of the electrode 34 lies approximately on the axis of the conduit 14 within the pipe section 24. The electrode 34 is provided with a substantially rectangular cut-out extending radially therethrough in a direction parallel to the air flow along the conduit 14, as indicated by the broken lines in FIG. 1, and also in FIG. 2 discussed in more detail below. We have found that this form of electrode gives good sensitivity without offering substantial resistance to air flow along the air conduit 14.

In addition, the form of the electrode 34 means that only a small aperture has to be cut in the wall of the pipe 12 in order to install the electrode in the pipe. In theory, this might suggest that an existing vehicle's system could be retro-fitted with an apparatus of the invention merely by cutting the small aperture necessary for insertion of the electrode 34 into some part of the existing air intake system without dismantling that system. However, we specifically do not recommend attempting to install an electrode in an existing air intake system without dismantling the system since there is a very grave risk that cutting the necessary aperture in the system will leave small metal particles within the system, and such small metal particles may eventually be swept by the air flow through the system into the engine or other gas-consuming device, with potentially disastrous results. Accordingly, if the instant apparatus is to be retrofitted into an existing air intake system, we recommend that the component of the system in which the electrode is to be installed be removed from the system before cutting the necessary aperture therein. Care should be taken to remove any metal or other filings resulting from the cutting of the aperture before the component is reassembled into the air intake system. However, the form of the electrode 34 may be useful where it is desired to offer the instant apparatus as an optional extra on, for example, a motor vehicle. The air intake system can be produced with the appropriate small aperture (and, if desired, with the sleeve 38 already fixed in the appropriate part of the air intake system). Thereafter, the vehicles may be supplied with the apparatus already installed, or simply with a plug closing the appropriate aperture, this plug being readily removable if it is desired to retrofit the vehicle with an electrode.

The apparatus 10 operates as follows: when the engine 18 is operating, air is drawn through the filter 16 and along the conduit 14. As the air flow passes the needle member 26, the ions of both charges emitted from the needle member 26 neutralize substantially all charges on the incoming particles. After this neutralization, the air and the entrained particles pass through the curved pipe section 22 where the larger particles are triboelectrically charged. The mechanism of this triboelectric charging may be seen by considering the particle paths S and L in FIG. 1, these paths S and L representing typical tracks for a small and a large particle respectively. As shown in FIG. 1, the small and the large particles follow the same straight track along the conduit 14 within the pipe section 20. However, when the conduit 14 curves within the curved pipe section 22, two opposing forces act on the particles, namely the frictional forces imposed by the gas flow (which tend to make the particles follow a curved path following the curve of the pipe section 22) and inertial forces (which tend to make the particles follow a straight path parallel to the axis of the pipe section 20). In the case of the small particle, the ratio of frictional to inertial forces is relatively large, so the small particle travels along the track S essentially following the movement of the air surrounding it and does not come into contact with the walls of the curved pipe section 22. On the other hand, in the case of the large particle, the ratio of frictional to inertial forces is much smaller, and the inertial forces tend to prevail so that the particle proceeds substantially parallel to the axis of the pipe section 20 and eventually collides with the outer wall of the curved pipe section 22, as shown by the track L. After one or more collisions with the outer wall of the pipe section 22, the momentum of the large particle parallel to the axis of the pipe section 20 will be destroyed and thus the large particle will finally travel down the pipe section 24 past the electrode 34. However, the collisions between the large particle and the walls of the curved pipe section 22 will cause friction between the particle and the wall, resulting in triboelectric charging of the large particle, which will thus be charged as it passes the electrode 34.

Accordingly, notwithstanding the neutralization of all preexisting charges by the ionizer assembly, the air flow past electrode 34 will contain charged large particles which have undergone triboelectric charging in the curved pipe section 22. The flow of air containing the charged large particles along the conduit 14 past the electrode 34 creates a flow of space charge within this conduit and this space charge deposits charged particles on the electrode 34, thereby causing a current flow from the electrode 34 through the current measuring means 44 and the line 46 to ground; however, for the reasons discussed above, this current will be determined only by the concentration of the large particles in the air flow since the small particles are not subject to triboelectric charging. While the filter 16 is operating normally, the current passing through the current measuring means 44 will remain below a predetermined level and the servomechanism 48 will keep the valve 50 in the open position shown in FIG. 1 so that air flow to the engine 18 is not interrupted. If, however, for any reason (e.g. perforation of the filter 16) the concentration of large particles in the air flow along the conduit 14 becomes too great, the current passing through the current measuring means 44 will exceed a predetermined value. When the current measuring device 44 registers this excessive current, it sends a signal to the servomechanism 48 which closes the valve 50, thus cutting off the flow of dirty air to the engine 18 before the engine can become damaged. In addition, the current measuring device 44 sends a signal along the line 51 to shut down the engine in any appropriate manner. Finally, the current measuring device 44 causes a current flow through the lamp 52 thus illuminating this lamp and advising the driver of the vehicle that the filter 16 has failed.

It will be appreciated that, when the instant apparatus is being used in certain types of vehicles (for example, highway trucks), the sudden shutdown of the engine 18 just described could be dangerous. Accordingly, when the engine 18 is of a type which can tolerate a short period of operation on dusty air without significant damage, it may be desirable to use a form of current measuring device 44 which gives an instant warning of failure of the filter 16 (by illuminating the lamp 52), but does not interrupt the air flow to the engine for a limited period (for example, 30 seconds), thus giving the driver a period in which to stop the vehicle without the engine being shut down.

The second embodiment of the invention shown schematically in FIG. 2 uses the same type of filter, ionizer and charge meauring means as the first embodiment shown in FIG. 1. (The servo mechanism, valve, engine control line 51 and warning lamp are omitted from FIG. 2 for the sake of simplicity.) However, in the embodiment shown in FIG. 2 the engine 18 is turbocharged and the triboelectric charging means comprises the compressor 70 of the engine turbocharger. It will be apparent to those skilled in the art that the rapid rotation of the blades of the turbocharger compressor effects triboelectric charging of the large particles of the gas in a manner generally similar to that described above with reference to the apparatus shown in FIG. 1. More specifically, as the air approaches the blades of the compressor 70, the air flow is deflected sideways by the blades. The effect of this sideways deflection of air by the compressor blades has an effect very similar to the deflection of the air flow by the curved section 22 of the pipe 12 shown in FIG. 1. In the case of small particles, the ratio of frictional to inertial forces is relatively large, so that the small particles tend to closely follow the flow of air, and consequently most of the small particles are deflected sideways with the air flow without coming into contact with the compressor blades or with the compressor housing. On the other hand, in the case of large particles the ratio of frictional to intertial forces is relatively large, so that the large particles tend to continue in a straight line and do not closely track the sideways deflection of the air flow. Consequently, the large particles are much more likely to come into contact with the compressor blades or housing and undergo triboelectric charging than the small particles. Indeed, in most cases a turbocharger compressor will be considerably more effective in triboelectric charging than a curved section of an air intake pipe. It will also be apparent that the apparatus shown in FIG. 2 can be retro-fitted relatively easily to an existing turbocharged engine air intake system, since it is only necessary to cut small apertures in the existing air intake ducts to install the ionizer assembly and electrode.

FIG. 3 shows a partial circuit diagram of the current measuring device 44 shown in FIGS. 1 and 2. FIG. 3 shows the amplifying part of the current measuring device connected to a bar graph light emitting diode (LED) array which provides a visual indication of the current passing through the currentmeasuring device and which can, if desired, be provided instead of or in addition to the warning lamp 52. The switching circuits necessary to activate the servomechanism 48, the warning lamp 52, and the engine control line 51 are not shown in FIG. 3 since they are entirely conventional and appropriate circuits will readily be apparent to those skilled in the art.

The circuit shown in FIG. 3 is powered from a 24 V D.C. supply applied between a positive supply line 100 and a return line 102. The lines 100 and 102 are connected, via a four-pin connector 104, to pins 1 and 14 respectively of a voltage stabilization circuit 106, which is an Integrated Circuits DIP 24 1212DB integrated circuit. This integrated circuit produces a +12 V output on its pin 6 which is connected to a positive supply line 108, a −12 V output on its pin 7 which is connected to a negative supply line 110, and a common or ground output at its pin 9 which is connected to a ground line 112. A smoothing capacitor C1 is connected between the positive supply line 108 and the ground line 112, while a second smoothing capacitor C2 is similarly connected to the negative supply line 110 and the ground line 112.

The input to the current measuring device from line 28 (FIG. 1) is received at a socket 114, one terminal of this socket being connected via a resistor R1 to the negative input (pin 2) of an integrated circuit U1. (To provide the necessary input impedance, resistor R1 preferably has a value of the order of $10^{10}$ ohms.) This integrated circuit U1 is an Intersil ICH 8500 ACTV amplifier circuit, which is an electrometer amplifier circuit having a very high input impedance. The positive input (pin 3) of integrated circuit U1 and pin 8 thereof are connected directly to the ground line 112, pin 4 is connected directly to the negative supply line 110, and pin 7 directly to the positive supply line 108. A capacitor C3 is connected between pins 7 and 8 (thus bridging the positive supply and ground lines 108 and 112 respectively) while a further capacitor C4 is connected between pins 4 and 8, thus bridging the negative supply and the ground lines 110 and 112 respectively. Finally, pins 1 and 5 of integrated circuit U1 are bridged by resistance R2, which forms a part of a potentiometer, the movable terminal of this potentiometer being connected to the negative supply line 110.

The output from integrated circuit U1 appears at pin 6. A variable feedback loop is provided for integrated circuit U1, the output from pin 6 of U1 being supplied to a three-position switch S1 which can be used to place any one of three different resistors R3, R4 and R5 in series with resistor R1 between pins 6 and 2 of integrated circuit U1. By selecting different ones of the resistors R3, R4 and R5, the range of current measured by the circuit can be varied. The output of pin 6 of U1 is also supplied via a resistor R6 to a line 116 which is connected to the removable terminal of a two-position selector switch S2a. This switch can be used to place one of the two resistors R7 and R8 in series with R6. The common output of R7 and R8 is connected to a common input of two resistors R9 and R10, one of which can be selected by a switch S2b which is ganged with S2a so that either R7 or R9 or R8 and R10 can be placed in series with R6. The output from switch S2b is conveyed by a line 118 to a positive input (pin 3) of an integrated circuit U2. Capacitors C5 and C6 connect the ground line 112 to the lines 116 and 118 respectively; thus, C5 and C6 together with the resistors R7/R8 and R9/R10 respectively, form two RC circuits which effect low-pass filtering of the output from U1 before it reaches U2.

The integrated circuit U2 actually comprises one-half of a Texas Instruments TLO 72 double linear amplifier integrated circuit, the other half of this double amplifier being the integrated circuit U3 described below. As is conventional, power supply connections to the double amplifier are only shown on one of the amplifier components, in this case U3. To provide a variable negative input for U2, resistors R11, R12 and R13 are arranged in series as a voltage divider between the positive and negative supply lines 108 and 110 respectively and an appropriate voltage which can be varied by the operator, is tapped from R12 and fed via a resistor R14 to the negative input (pin 2) of U2. This tapping of the variable voltage from R12 enables the amplifier U2 to be adjusted for any offset on the incoming signal due to e.g. small leakage currents even when no dust is present in the air flowing along the conduit 14 (FIG. 1). The output of U2 appears at pin 1 thereof and, to establish appropriate feedback, this output is fed via a resistor R15 to pin 2 thereof and via a capacitor C7 to the common input of resistors R9 and R10. The output from pin 1 of U2 is also fed to the movable terminal of a five-position selector switch S3, which places one of five different resistors R16, R17, R18, R19 and R20 between the output of U2 and a line 120 connected to the positive input (pin 5) of the aforementioned integrated circuit amplifier U3. An RC circuit comprising a capacitor C7 in parallel with a resistor R21 is connected between the line 120 and the ground line 112. The negative input (pin 6) of U3 is connected via a resistor R22 to the ground line 112. The positive and negative power supply inputs, pins 8 and 4 respectively, of U3 are connected to the positive and negative supply lines 108 and 110 respectively; those pins 8 and 4 are also connected via capacitors C8 and C9 respectively to the ground line 112. The switch S3 and the associated resistors R16/R20 allow adjustment of the overall gain provided by the amplifiers U2 and U3.

The output from U3 appears at pin 7 thereof. To provide proper feedback, this output is fed back via an RC circuit comprising a capacitor C10 connected in parallel with a resistor R23 to the negative input (pin 6) of U3. The output from U3 is also fed via a signal line 122 and the 4-pin connector 104 to a bar graph LED array 124, which is of the commercially available National Semiconductor Model NSM 3914 type. A signal return line 126 from the array 124 is connected by the 4-pin connector 104 to the ground line 112.

It will thus be seen that the circuit shown in FIG. 6 provides a three-stage amplification of the incoming signal from the socket 114, these three stages of amplification being effected by the integrated circuits U1, U2 and U3 respectively. The circuit provides for adjustment of range, offset, and gain by means of the switch S1, the variable voltage applied to the negative input of amplifier U2, and the switch S3 respectively and also provides for filtering of the incoming signals by the RC circuits formed by the capacitors C5 and C6 in association with the resistors R7/R8 and R9/R10 respectively. Thus, the circuit shown in FIG. 6 converts the very small currents, of the order of $10^{-12}$ to $10^{-13}$ amps. flowing through the resistor R1 and the socket 114 to a varying voltage on line 122 sufficient to drive the LED array 124.

The circuit shown in FIG. 3 is an experimental prototype and is deliberately provided with variable range, filter and gain settings in order to enable it to be used with a variety of types of apparatus of the invention. Those skilled in the art will appreciate that production models of such a circuit, intended only for use with one particular type of electrode in a specific vehicle or other environment, will not normally require such variability, thus permitting considerable simplification of the circuitry; in such an invariable production model, a single resistor could replace the resistors R3, R4 and R5 and the switch S1, a second single resistor could replace the switch S2 and the resistors R7, R8, R9 and R10, while a third single resistor could replace the switch S3 and the resistors R16–R20.

Although the circuit shown in FIG. 3 has been described above as a current measuring circuit, it can readily be modified to act as a pulse detecting circuit merely by changing the values of certain components. As will be appreciated from the description given above as to mode of operation of both the pulse counting and current measuring types of the instant apparatus, the current actually induced in a line connecting the electrode 34 (FIG. 1) to ground will be the same in both cases, the signal comprising a direct current caused by the deposition of charged particles on the electrode, but superimposed upon this direct current will be "spikes" or pulses produced by induction of the charges on the electrode as dust particles pass the electrode 34 without being deposited thereon. Thus, a current measuring circuit used in the instant apparatus should be equipped with a low-pass filter with a cut-off frequency sufficiently low to eliminate the pulses in the incoming signal; in practice, this cut-off frequency is preferably about 1 Hz. In the circuit shown in FIG. 3, a cut-off frequency of about 1 Hz. can be achieved by using resistors R8 and R10 of about 1 megaohm, giving C5 a value of 2.2 microfarad and capacitor C6 a value of 1 microfarad. In fact, the cut-off frequency of the circuit shown in FIG. 3 is in practice regulated not only by the RC circuits formed by the capacitors C5 and C6 together with the resistors R7–R10, but also by the input resistor R1. To provide a high input resistance to the circuit, we prefer to make the resistor R1 about $10^{10}$ ohms, and such a resistor will have an inherent capacity of about 10 picofarad. Thus, resistor R1 alone acts as a filtering RC circuit with a cut-off frequency of around 2 Hz.

Obviously, to modify the circuit shown in FIG. 3 so that it acts as a pulse counting circuit, it will be necessary to raise the cut-off frequency of the circuit. This may conveniently be done by reducing R1 to about $10^8$ ohms, and reducing resistors R8 and R10 to about 100 kiloohms thereby raising the cut-off frequency to around 10 Hz. Those skilled in the art will also appreciate that it will be necessary to pass the output from the circuit shown in FIG. 3 to a conventional pulse counting device rather than to a bar graph array.

The apparatus of the invention is small, rugged, relatively insensitive to vibration, requires little power and is able to distinguish between large and small particles in the gas flow, thus avoiding false alarms due to very small particles which will not harm a gas-using device attached thereto.

It will be apparent to those skilled in the art that numerous changes and modifications can be made in the preferred embodiments of the instant apparatus and method already described without departing from the scope of the invention. Accordingly, the foregoing description is to be construed in an illustrative and not in a limitative sense, the scope of the invention being defined solely by the appended claims.

We claim:
1. Apparatus for measuring the concentration of large particles in a gas containing both large and smaller particles comprising:
   a charge neutralizing device for neutralizing pre-existing charges on particles in said gas;
   a triboelectric charging means for effecting triboelectric charging of said large particles in said gas after said gas has passed said charge neutralizing device; and
   charge measuring means for measuring charges on particles in said gas after said gas has passed said triboelectric charging means.
2. Apparatus according to claim 1 wherein said triboelectric charging means comprises a conduit member having walls defining a conduit through which said gas can flow, at least part of said conduit being curved.
3. Apparatus according to claim 1 wherein said triboelectric charging means comprises a conduit member having walls defining a conduit through which said gas can flow and a rotatable member disposed within said conduit.
4. Apparatus according to claim 3 wherein said triboelectric charging means comprises a turbocharger.
5. Apparatus according to claim 1 wherein said charging neutralizing device comprises an alternating current ionizer.
6. Apparatus according to claim 1 wherein said charge measuring means comprises:
   a conduit member formed of electrically-conductive material and having walls defining a conduit through which said gas can flow;
   an electrode at least part of which is disposed within said conduit;
   an insulator disposed between said conduit member and said electrode, thereby electrically insulating said electrode from said conduit member;
   current measuring means electrically connected to said electrode; and
   potential maintaining means for maintaining said conduit member and said electrode at substantially the same potential.
7. Apparatus according to claim 6 wherein said potential maintaining means comprises a connection between said conduit member and ground and a connection between said current measuring means and ground such that current from said electrode will flow through said current measuring means to ground.
8. Apparatus according to claim 6 wherein said electrode has the form of an elongate rod extending part-way across said conduit in a direction substantially perpendiculer to the flow of gas therealong.
9. Apparatus according to claim 8 wherein said electrode has the form of a cylinder having its axis substantially perpendicular to said flow of gas, said cylinder having walls defining an aperture passing through said cylinder in a direction substantially parallel to said flow of gas.
10. Apparatus according to claim 1 wherein said charge measuring means comprises:
    a conduit member formed of electrically-conductive material and having walls defining a conduit through which said gas can flow;
    an electrode at least part of which is disposed within said conduit;
    an insulator disposed between said conduit member and said electrode, thereby electrically insulating said electrode from said conduit member;
    pulse counting means electrically connected to said electrode; and
    potential maintaining means for maintaining said conduit member and said electrode at substantially the same potential.
11. Apparatus according to claim 10 wherein said potential maintaining means comprises a connection between said conduit member and ground and a connection between said current measuring means and ground such that current from said electrode will flow through said current measuring means to ground.
12. Apparatus according to claim 10 wherein said electrode has the form of an elongate rod extending part-way across said conduit in a direction substantially perpendicular to the flow of gas therealong.
13. Apparatus according to claim 12 wherein said electrode has the form of a cylinder having its axis substantially perpendicular to said flow of gas, said cylinder having walls defining an aperture passing through said cylinder in a direction substantially parallel to said flow of gas.
14. Apparatus according to claim 1 further comprising a filter for removing particles from said gas before it enters said triboelectric charging means.

15. Apparatus according to claim 1 further comprising a gas receiving device which receives said gas after said gas has passed said charge detection means and cut-off means for preventing damage to said gas receiving device whenever said charge measuring means indicates that the concentration of said large particles in said gas exceeds a predetermined value.

16. Apparatus according to claim 15 wherein said gas receiving device is an engine and said cut-off means comprises means for preventing gas passing said charge detection means from reaching said engine.

17. Apparatus according to claim 16 wherein said engine is provided with a turbocharger which serves as said triboelectric charging means.

18. Apparatus according to claim 16 wherein said cut-off means further comprises means for providing a warning signal.

19. Apparatus according to claim 15 wherein said cut-off means further comprises means for stopping said engine.

20. A method of measuring the concentration of large particles in a gas containing both large and smaller particles comprising:
   neutralizing any pre-existing charges on particles in said gas;
   thereafter passing said gas through a triboelectric charging means, thereby effecting triboelectric charging of said large particles in said gas; and
   thereafter measuring the charges on particles in the gas.

21. A method according to claim 20 wherein said triboelectric charging means comprises a conduit member having walls defining a conduit through which said gas can flow, at least part of said conduit being curved.

22. A method according to claim 20 wherein said triboelectric charging means comprises a turbocharger.

* * * * *